(12) United States Patent
Jones

(10) Patent No.: US 9,324,550 B1
(45) Date of Patent: Apr. 26, 2016

(54) SELF-SHIELDING FLEX-CIRCUIT DRIFT TUBE, DRIFT TUBE ASSEMBLY AND METHOD OF MAKING

(71) Applicant: Sandia Corporation, Albuquerque, NM (US)

(72) Inventor: David Alexander Jones, Sandia Park, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/615,263

(22) Filed: Feb. 5, 2015

Related U.S. Application Data

(60) Provisional application No. 61/936,774, filed on Feb. 6, 2014.

(51) Int. Cl.
| | |
|---|---|
| *H01J 49/40* | (2006.01) |
| *H01J 49/06* | (2006.01) |
| *G01N 27/62* | (2006.01) |
| *H01J 49/00* | (2006.01) |

(52) U.S. Cl.
CPC ............ *H01J 49/062* (2013.01); *G01N 27/622* (2013.01); *H01J 49/0022* (2013.01)

(58) Field of Classification Search
USPC ........ 250/281, 282, 283, 290, 291, 292, 293, 250/294, 295, 296, 297, 298, 299
See application file for complete search history.

(56) References Cited

U.S. PATENT DOCUMENTS

| | | | |
|---|---|---|---|
| 2008/0073514 A1* | 3/2008 | Landgraf | ............. G01N 27/622 250/290 |
| 2014/0262971 A1* | 9/2014 | Drumheller | ................ 209/127.1 |

* cited by examiner

*Primary Examiner* — Nicole Ippolito
(74) *Attorney, Agent, or Firm* — Daniel J. Jenkins

(57) ABSTRACT

The present disclosure is directed to an ion mobility drift tube fabricated using flex-circuit technology in which every other drift electrode is on a different layer of the flex-circuit and each drift electrode partially overlaps the adjacent electrodes on the other layer. This results in a self-shielding effect where the drift electrodes themselves shield the interior of the drift tube from unwanted electro-magnetic noise. In addition, this drift tube can be manufactured with an integral flex-heater for temperature control. This design will significantly improve the noise immunity, size, weight, and power requirements of hand-held ion mobility systems such as those used for explosive detection.

18 Claims, 12 Drawing Sheets

SELF-SHIELDING FLEX-CIRCUIT DRIFT TUBE, DRIFT TUBE ASSEMBLY AND METHOD OF MAKING

RELATED APPLICATIONS

This application claims priority to U.S. Provisional Patent Application No. 61/936,774, filed on Feb. 6, 2014, and entitled "SELF-SHIELDING FLEX-CIRCUIT DRIFT TUBE FOR ION MOBILITY SPECTROMETRY," the entirety of which is incorporated herein by reference.

GOVERNMENT RIGHTS

This invention was made with Government support under Contract No. DE-AC04-94AL85000 between Sandia Corporation and the U.S. Department of Energy. The Government has certain rights in the invention.

BACKGROUND

Ion mobility spectrometry (IMS) is an analytical technique used to identify ionized molecules in the gas phase based on their mobility in a gas. In time-of-flight IMS, pulses of ions are accelerated by a voltage gradient along a drift tube and the migration time (drift time), which is characteristic of different ions, is recorded by a detector at the end of the drift tube. Typically, drift tubes are composed of alternating electrode (metal) and insulator (ceramic, plastic) rings.

Stacked alternating electrode and insulator designs have a number of drawbacks. Stacked drift tubes must be manufactured from machined components which are difficult and time consuming to produce, especially insulators made from machineable ceramics. Machineable ceramics are expensive, typically require dedicated equipment such as diamond tools, are more prone to breaking during machining and do not hold tolerances well when compared with traditionally machined materials (brass, aluminum, steel). The ceramic components of drift tubes are also more prone to breakage during use (e.g. if it is dropped). The wall thickness of both the electrode and insulator components needs significant wall thickness for mechanical stability. This results in a heavy and large outer diameter drift tube relative to the size of ion path (especially important in portable, handheld applications), and a high thermal mass which requires a significant time to heat to operating temperature and cool when the system is put in a non-operational state. The stacked drift tube designs also require some sort of support structure to keep all of the components in contact with each other as well as conductive enclosure surrounding the drift tube (a Faraday cage) that prohibits perturbation of the drift tube's electric field from an external potential, each of which add to the size and weight of the assembly. Stacked drift tubes also have interfaces between the various stacked components that create crevices, cracks or junctions that result in trapped analyte carrying over from one analytical run to the next. Back-diffusion of room air into a stacked drift tube can also cause contamination in the IMS drift tube.

What is needed is an ion mobility drift tube that provides improved noise immunity, ruggedness and manufacturability while reducing size, weight, and power requirements.

SUMMARY

The present disclosure is directed to self-shielding flex-circuit drift tubes for ion mobility spectrometry. In an embodiment, the present disclosure provides ion mobility drift tubes using flex-circuit technology in which every other drift electrode is on a different layer of the flex-circuit and each drift electrode partially overlaps the adjacent electrodes on the other layer. The disclosed drift tubes provide for a self-shielding effect where the drift electrodes themselves shield the interior of the drift tube from unwanted electromagnetic noise. The disclosed drift tubes provide for improved noise immunity, ruggedness and manufacturability while reducing size, weight, and power requirements over the prior art. In an embodiment, the drift tubes can include an integral flex-heater for temperature control. This embodiment significantly improves the noise immunity, size, weight, and power requirements of hand-held ion mobility systems such as those used for explosive detection.

According to an embodiment of the disclosure, a drift tube is disclosed that includes a flexible, nonconductive substrate comprising a top surface, a bottom surface and a tube portion having a tubular geometry, and a plurality of outer conductive electrodes disposed on and in contact with the top surface of the tube portion, and a plurality of inner conductive electrodes disposed on and in contact with the bottom surface of the tube portion.

According to another embodiment of the disclosure, a drift tube assembly is disclosed that includes a drift tube having a flexible, nonconductive substrate comprising a top surface, a bottom surface and a tube portion having a tubular geometry, and a plurality of outer electrodes disposed on and in contact with the top surface of the tube portion, and a plurality of inner electrodes disposed on and in contact with the bottom surface of the tube portion, and an aperture grid, ion gate and extractor grid disposed with the tube portion.

According to another embodiment of the disclosure, a method of making a drift tube is disclosed that includes providing a flexible, nonconductive substrate comprising a top surface and a bottom surface, forming outer electrodes on the top surface and inner electrodes on the bottom surface of a tube portion of the flexible, nonconductive substrate, and forming the tube portion into a tube geometry having an inner central axis so that the top surface is further away from the inner central axis than the bottom surface.

Additional features and advantages are described herein, and will be apparent from the following Detailed Description and the figures.

DETAILED DESCRIPTION

The present disclosure is directed to drift tubes, drift tube assemblies and methods of making drift tubes. The drift tubes of the present disclosure utilize flex circuit technology that make the drift tubes self-shielding. The drift tubes include a flexible substrate of one or more layers of a flexible substrate material. As used herein, the term "flexible" is understood by the plain meaning of the term in addition to the ability to be rolled into a tube or tube geometry at ambient or room temperature without breaking cracking, kinking or creasing. In an embodiment, the substrate can be rolled at ambient temperature to form a tube having a diameter of between 1/8 inch and 10 inches in diameter without breaking, cracking, kinking or creasing. The disclosed drift tubes provide for improved noise immunity, ruggedness and manufacturability while reducing size, weight, and power requirements over the prior art.

The disclosed drift tubes and drift tube assemblies may be used for ion mobility spectrometry (IMS), as reflectron tubes in time-of-flight mass spectrometry, as components of ion guides and collision cells for mass spectrometry, for the study of ion-molecule reaction kinetics and thermodynamics, in proton transfer reaction mass spectrometry, for the detection of high energy particles such as cosmic rays and other ion detection systems and techniques.

Figure 1:
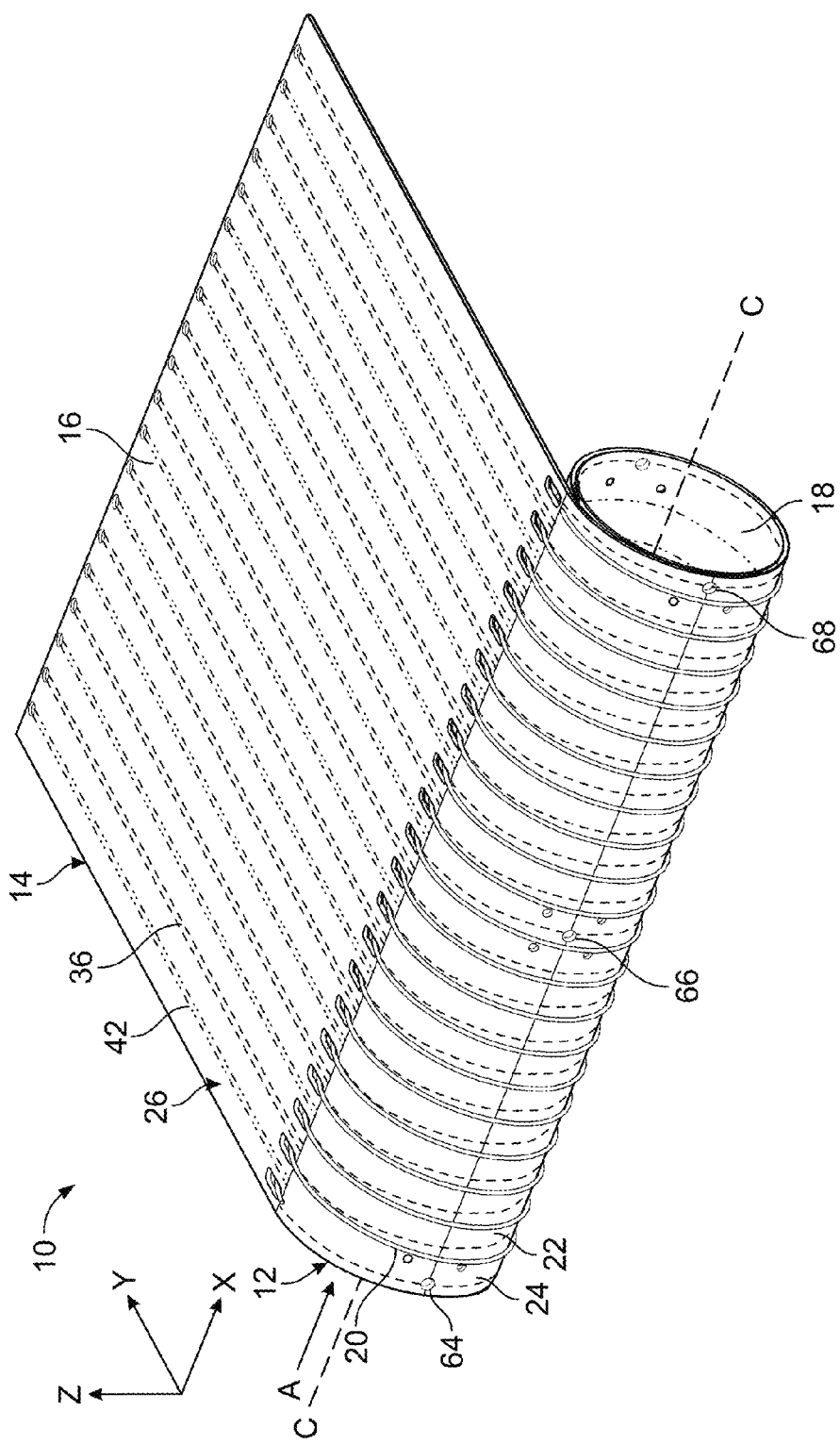
FIG. 1 shows a perspective view of an embodiment of a drift tube according to the disclosure.
Figure 2:
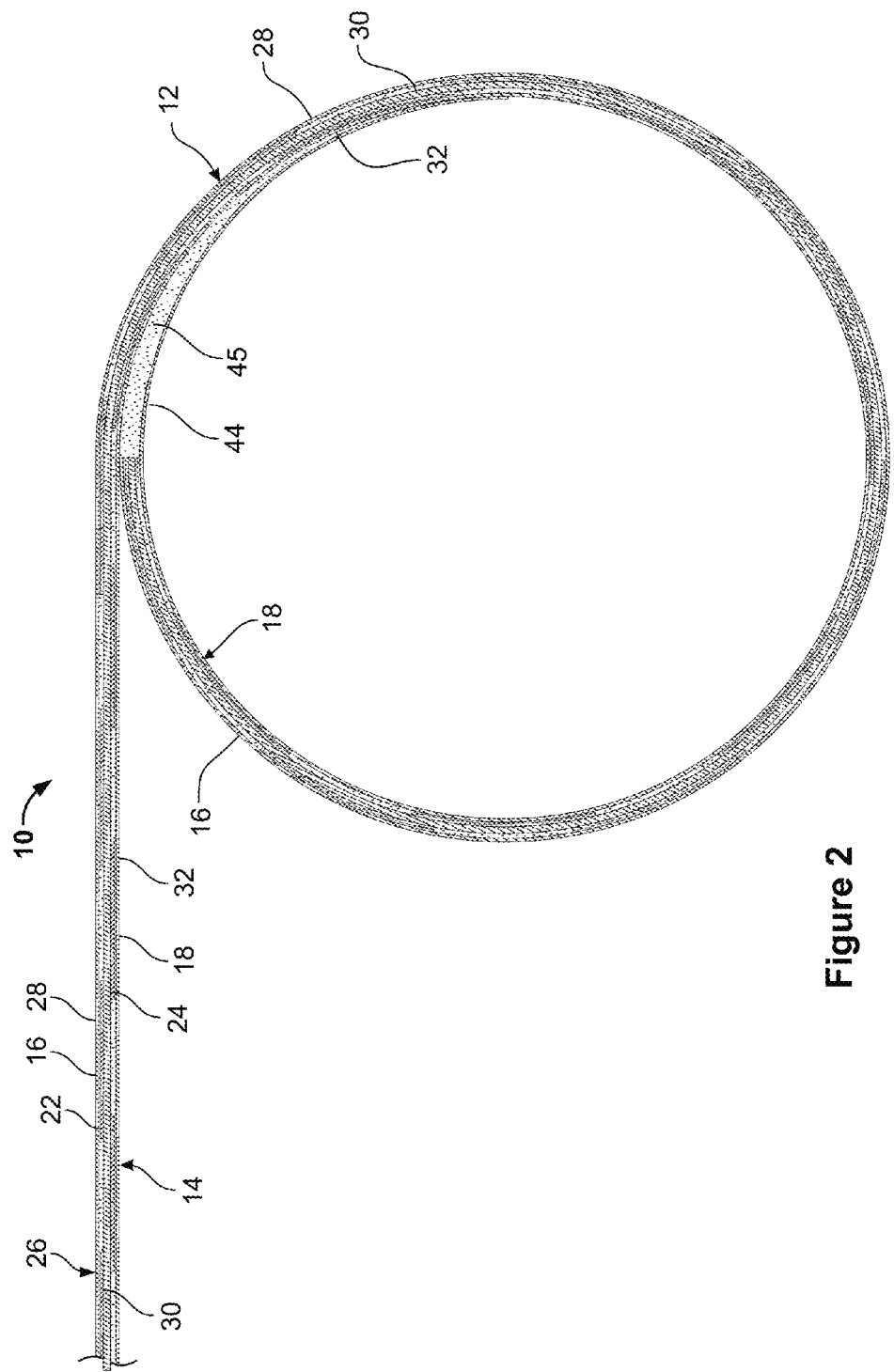
FIG. 2 shows an end view of the drift tube of FIG. 1 taken from direction A.

FIGS. 1 and 2 illustrate an embodiment of a drift tube 10 according to an embodiment of the disclosure. The drift tube 10 includes a tube portion 12 and a circuit leads portion 14. The tube portion 12 has a tubular geometry around a central axis C. The circuit leads portion 14 has a flat or planar geometry. In another embodiment, the circuit leads portion 14 may have geometry, such as folded, flat, bent, curved or other geometry selected to provide electrical connectivity to a select application. The drift tube 10 includes an outer surface 16, which may be referred to as a first surface or top surface, and an inner surface 18, which may be referred to as a second surface or bottom surface. In this exemplary embodiment, the drift tube 10 further includes a heater 20.

The tube portion 12 includes a plurality of outer electrodes 22 and inner electrodes 24 embedded in a flexible matrix 26. The circuit leads portion 14 includes a plurality of outer and inner circuit leads 36, 42 attached to outer and inner electrodes 22, 24. The plurality of outer and inner circuit leads 36, 42 are also embedded in the flexible matrix 26.

Figure 3:
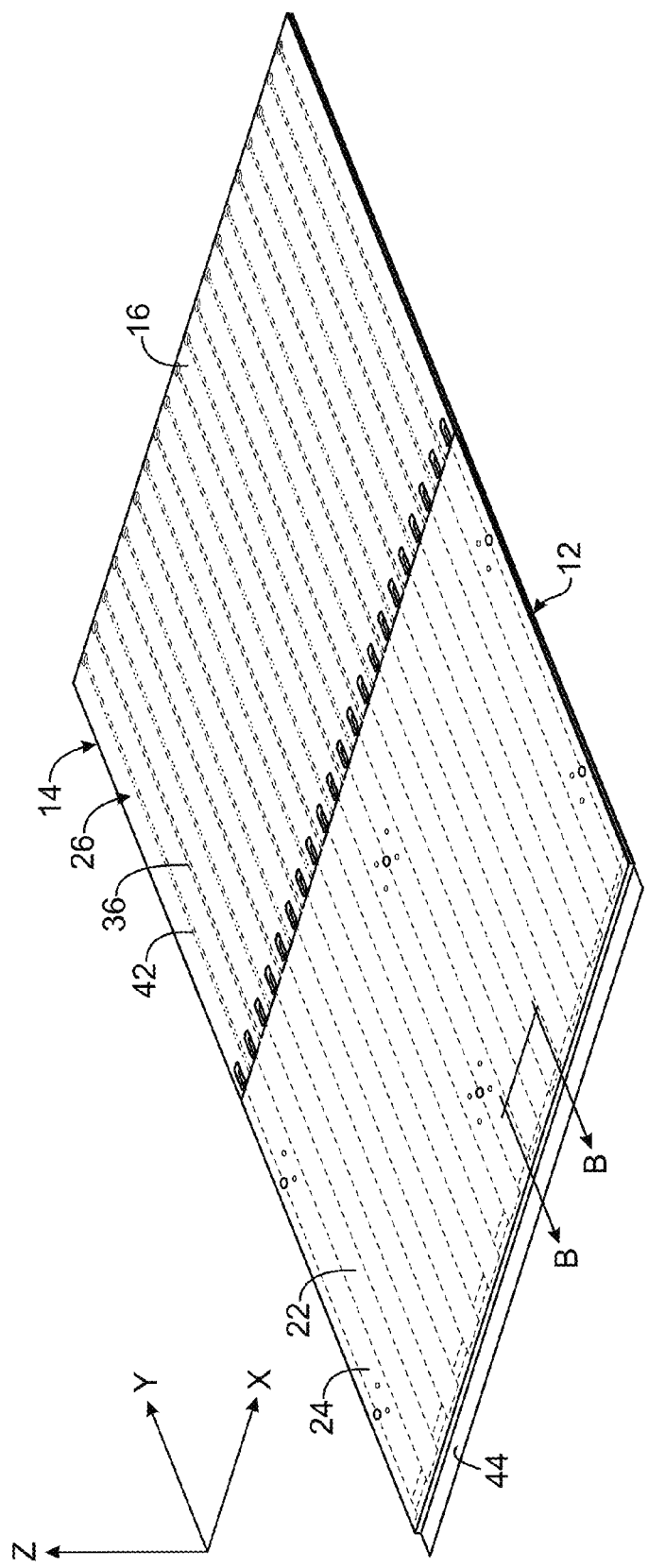
FIG. 3 shows a top view of the drift tube of FIG. 1 before rolling and having the heating element removed.
Figure 4:
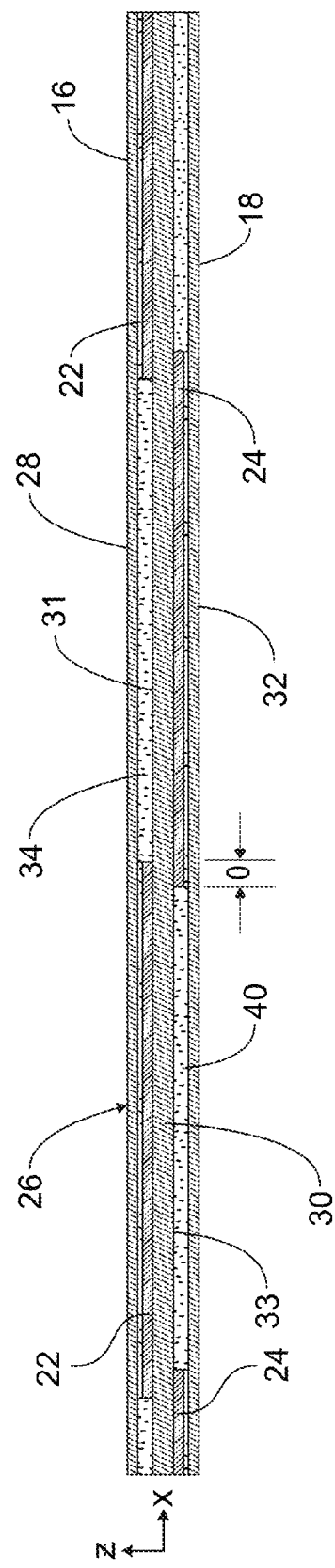
FIG. 4 illustrates a partial cut away end view of the drift tube of FIG. 1 before rolling.

FIG. 3 illustrates the drift tube 12 before the tube portion 12 is rolled into the tube geometry as shown in FIG. 1. FIG. 4 illustrates a cross section of a portion of the tube portion 12. As can be seen in FIG. 4, the flexible matrix 26 includes a top or outer layer 28, a center or substrate layer 30, and a bottom or inner layer 32. In this exemplary embodiment, the outer, substrate and inner layers 28, 30, 32 are a single layer of material. In another embodiment, the outer, substrate and inner layers 28, 30, 32 may be formed of one or more or a plurality of layers of material.

In this exemplary embodiment, the flexible matrix 26 is formed of a single, flexible, insulating, nonconductive material. The flexible material may be a polymer or epoxy. The polymer may be, but is not limited to polyesters, polyimides, polyamides, polyetherimides, polyaryletherketones and fluropolymers. In an embodiment, the epoxy may be a fiber-reinforced laminate such as a glass-reinforced epoxy laminate. In an embodiment, the polymer may be, but is not limited to Kapton® (4,4'-oxydiphenylene-pyromellitimide), Teflon® (polytetrafluoroethylene), PEEK (polyether ether ketone), PEN (polyethylene napthalate), and Ultem® (polyetherimide). In an embodiment, the flexible material may include fillers, strength enhancers and rigidizers. In another embodiment, the flexible material may be formed of two or more layers of different flexible materials. For example, one or more of the outer, substrate and inner layers 28, 30, 32 may be formed of one or more layers of the same or different flexible materials. In an embodiment, the flexible matrix material may be transparent. In an embodiment, one or more of the layers forming one or more of the outer, substrate and inner layers 28, 30, 32 may be formed of a transparent material.

Referring again to FIG. 4, it can be seen that outer electrodes 22 are disposed between the outer layer 28 and the substrate layer 30. The outer electrodes 22 are disposed in the tube portion 12 of the drift tube 10 (see FIGS. 1 and 2). The outer electrodes 22 are formed of a conductive material on a top surface 31 of the substrate layer 30. In an embodiment, the conductive material may be a metal or metal alloy, such as, but not limited to copper, silver, gold, nickel, aluminum and alloys thereof. In this exemplary process, the outer electrodes 22 are formed upon the substrate layer 30 by a deposition process, such as, but not limited to electrodeposition, sputtering or spraying. In another embodiment, the outer electrodes 22 may be formed separately and attached to the substrate layer 30 by gluing or other joining method. In this exemplary embodiment, the outer electrodes 22 all have the same width in the X direction. In another embodiment, the outer electrodes 22 may have different widths.

Also disposed between the outer layer 28 and the inner substrate 30 is a top glue layer 34 that attaches the outer layer 22 to the outer electrodes 22 and substrate layer 30. The top glue layer 34 is an adhesive capable of bonding to both organic and metal components. The top glue layer 34 may be formed of an adhesive, such as, but not limited to polyimide, polyester, acrylic, epoxy, and phenolic adhesives. In an embodiment, the adhesive may be an acrylic and epoxy adhesives.

Also disposed between the outer layer 28 and the substrate layer 30 are a plurality of outer electrode leads 36 disposed in the circuit leads portion 14 (see FIGS. 1 and 3) that electrically connect the outer electrodes 22 to a corresponding plurality of electrical terminals 38 (see FIGS. 1 and 3). The outer electrode leads 36 and electrical terminals 38 are formed of similar materials and process as the outer electrodes 22. The top glue layer 30 extends into the circuit leads portion 14 (see FIGS. 1 and 3) between the outer layer 28 and the substrate layer 30 to bond or attach the outer layer 28 to the outer electrode leads 36 (see FIGS. 1 and 3) and the substrate layer 30.

Referring again to FIG. 4, it can be seen that inner electrodes 24 are disposed between the inner layer 32 and the substrate layer 30. The inner electrodes 24 are disposed in the tube portion 12 of the drift tube 10 (see FIGS. 1 and 2). The inner electrodes 24 are formed of a conductive material on a bottom surface 33 of the substrate layer 30. In an embodiment, the inner electrodes 24 may be formed of the same conductive material as the outer electrodes 22. In an embodiment, the conductive material may be a metal or metal alloy, such as, but not limited to copper, silver, gold, nickel, aluminum and alloys thereof. In this exemplary process, the inner electrodes 24 are formed upon the substrate layer 30 by a deposition process, such as, but not limited to electrodeposition, sputtering or spraying. In another embodiment, the inner electrodes 24 may be formed separately and attached to the substrate layer 30 by gluing or other joining method. In this exemplary embodiment, the inner electrodes 24 all have the same width in the X direction. In another embodiment, the inner electrodes 24 may have different widths. In this exemplary embodiment, the inner electrodes 24 have the same width in the X direction as the outer electrodes 22. In another embodiment, the inner and outer electrodes 24, 22 may have different widths.

Also disposed between the inner layer 32 and the substrate layer 30 is a bottom glue layer 40 that attaches the inner layer 32 to the inner electrodes 24 and substrate layer 30. The bottom glue layer 40 is an adhesive capable of bonding to both organic and metal components. In an embodiment, the bottom glue layer 40 is formed of the same adhesive material as the top glue layer 34. The bottom glue layer 40 may be formed of an adhesive, such as, but not limited to polyimide, polyester, acrylic, epoxy, and phenolic adhesives. In an embodiment, the adhesive may be an acrylic and epoxy adhesive.

Also disposed between the inner layer 32 and the inner substrate 30 are a plurality of inner electrode leads 42 disposed in the circuit leads portion 14 (see FIGS. 1 and 3) that electrically connect the inner electrodes 24 to a corresponding plurality of electrical terminals 38 (see FIGS. 1 and 3). The inner electrode leads 42 and electrical terminals 38 are formed of similar materials and process as the inner electrodes 24. The bottom glue layer 40 extends into the circuit leads portion 14 (see FIGS. 1 and 3) between the inner layer 32 and the substrate layer 30 to bond or attach the inner layer 32 to the inner electrode leads 42 (see FIGS. 1 and 3) and the substrate layer 30.

In another embodiment, one or more of the glue layers may be omitted between polymer and metal layers. In an embodiment, polymer to metal layers may be bonded or deposited by other methods, such as, but not limited to gluing, spraying, sputtering, and electrodeposition.

Referring again to FIGS. 2 and 3, it can be seen that the flexible matrix 26 further includes a lead tab section 44. In this exemplary embodiment, the lead tab section 44 is a portion of the inner layer 32. As can be seen in FIG. 2, the lead tab section 44 is attached or joined to the inner layer 32 so as to attach or join the tube portion 12 to itself to form the tube geometry for the tube portion 12. In this exemplary embodiment, the lead tab portion 44 is attached to the inner layer 32 by an adhesive or tab glue layer 45. In another embodiment, the lead tab section 44 may be attached or joined to the inner layer 32 by any known capable joining method for joining the flexible matrix material to itself, such as, but not limited to using adhesives, thermal welding, ultrasonic welding and soldering.

Referring again to FIG. 4, it can be seen that the outer electrodes 22 and inner electrodes 24 overlap "O" in the X plane. In this exemplary embodiment, the outer and inner electrodes overlap by approximately 5% of the width of the outer and inner electrodes 22, 24 in the X direction. In another embodiment, the outer and inner electrodes 22, 24 may overlap up to any extent that does not provide an electrical connection between adjacent electrodes. In another embodiment, the outer and inner electrodes 22, 24 may be coincident or may not overlap. However, the inventors have found that the best shielding of (minimum distortion of the electric field potentials inside the tube) from external electromagnetic interference occurs when a small overlap is present.

As discussed above and shown in FIG. 1, the drift tube 10 includes a heater 20. In this exemplary embodiment, the heater 20 is a resistance wire that is connected to a power source (not shown). In such a manner, the heater 20 sets desired operating temperature of the drift tube and maintains the temperature of the drift tube (typically within 1 degree C.) to ensure the reproducibility of IMS measurements.

Figure 5:
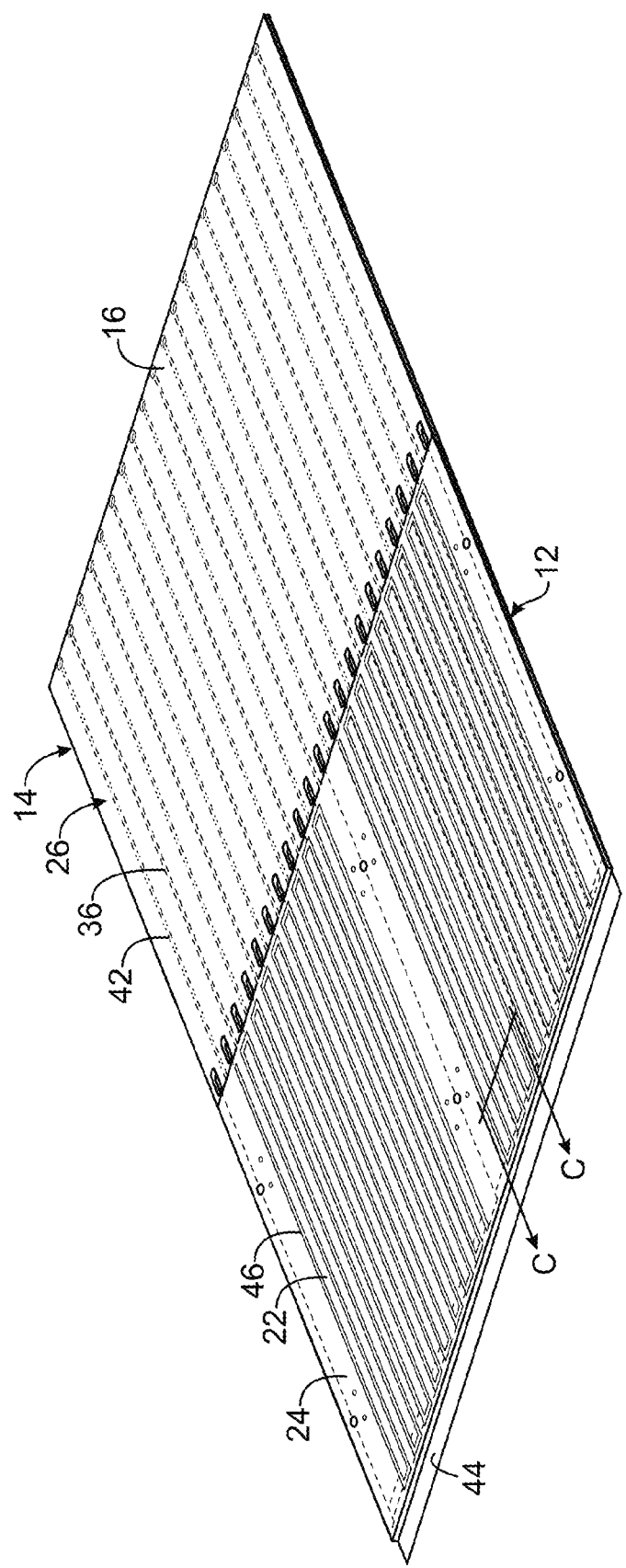
FIG. 5 illustrates another embodiment of a drift tube before rolling.
Figure 6:
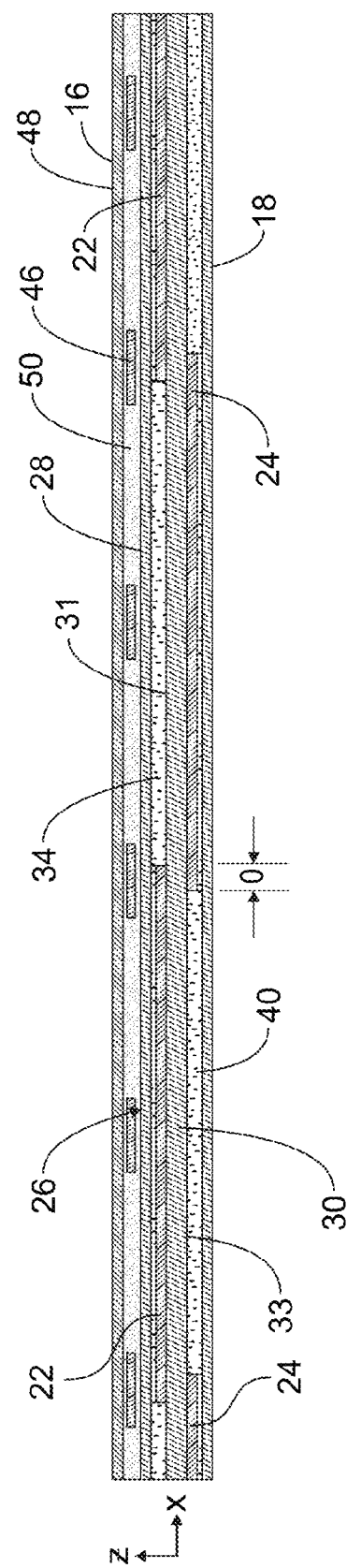
FIG. 6 illustrates a partial cut away end view of the drift tube of FIG. 5.

In another embodiment shown in FIGS. 5 and 6, the drift tube 10 may include an integral heater 46. The integral heater is also a resistance heater. In this embodiment, the X heater 46 is disposed between the outer layer 28 and a cover layer 48 in a cover glue layer 50 that attaches or bonds the cover layer 48 to the outer layer 28. The cover layer 48 may be formed of one or more of any of the materials that may be used to form all or part of the flexible matrix 26. Similarly, the cover glue layer 50 may be formed of any of the materials that may be used in either or both the top glue layer 34 and/or bottom glue layer 40.

These heaters make ion mobility measurements more accurate and reproducible by increasing precision because mobility is a function of temperature. In a poorly temperature controlled IMS, temperature gradients can exist across the tube that can impact the accuracy and reproducibility of the analyte's mobility from run to run, causing false results. If the temperature drifts due to poor temperature control, a resulting, uncontrolled change can occur in the mobility measurement, again leading to false results.

Compared to conventional drift tubes that are fabricated by stacking alternating electrodes and insulators the rolled flex circuit design has the following advantages:

1. Self-shielding. The overlapping electrode structure results in a self-shielding effect where the drift electrodes themselves shield the interior of the drift tube from unwanted electro-magnetic interference (EMI). Electric field simulations show that the electric field inside a conventional stacked drift tube is perturbed (see FIG. 2) when an external potential is present and is why Faraday cages are often employed to prevent perturbation by an external potential whereas no visible perturbation is observed in the self-shielding flex circuit drift tube (see FIG. 3).

2. Lightweight. The rolled flex circuit design is 10× (or more) lighter than conventional designs which is especially significant for hand held systems such as explosive detection systems.

3. Smaller. The rolled flex-circuit design has a significantly smaller wall thickness than conventional designs resulting in a much smaller outer diameter for the same inner diameter.

4. Self-supporting. By forming a tube and soldering/gluing at the seam, the drift tube becomes self-supporting. Most conventional designs need some form of support structure to maintain the integrity of the ring stack. This adds weight, size and complexity to the design and assembly.

5. Monolithic. The rolled flex-circuit design has only one seam and no other crevices, cracks or junctions that result in trapped analyte carrying over from one analytical run to the next.

6. Ease of manufacturing. The rolled flex circuit design can be manufactured in large quantities using conventional flex circuit fabrication techniques. Conventional tubes require machined components, often from exotic, expensive materials such as machineable ceramics.

7. Lower manufacturing cost. Since the rolled flex circuit design can be manufactured in large quantities using conventional flex-circuit fabrication techniques the per unit cost will be drastically reduced compared to conventional tubes which require machined components, often from exotic, expensive materials such as machineable ceramics.

8. Lower thermal mass. The small wall thickness of the rolled flex-circuit design means a much lower thermal mass than conventional tubes. This means much faster warm up times and bake-out cycles compared with conventional units.

9. Integral electronics. The rolled flex-circuit drift tube is fundamentally a printed circuit board so additional layers and traces can be added to accommodate electrical components such as temperature sensors and control circuitry.

10. Integral heaters. The rolled flex-circuit design can incorporate integral heaters which will eliminate the cold-spots that can occur in conventional designs that result in adsorbed analyte carrying over from one analytical run to the next. In addition, the integral nature of the heaters will make the design more energy efficient which is an important consideration in handheld systems.

11. Improved ruggedness. The rolled flex-circuit design is incredibly resistant to damage by shock or vibration compared to stacked ring designs made from brittle ceramics.

Figure 7:
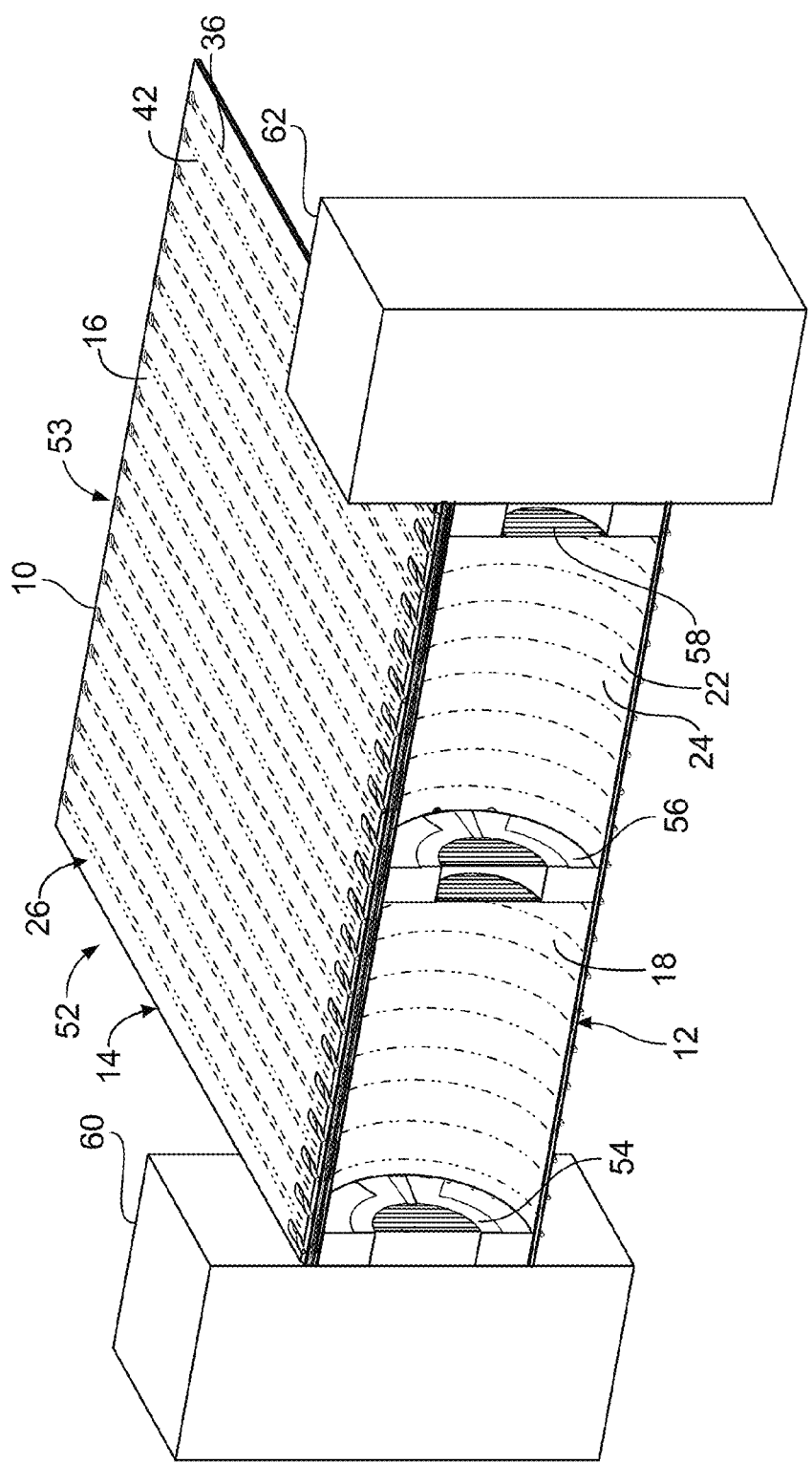
FIG. 7 illustrates an embodiment of a drift tube assembly according to the present disclosure.

FIG. 7 illustrates an embodiment of an ion mobility drift tube assembly 52 according to the present disclosure. As can be seen in FIG. 7, the ion mobility drift tube assembly 52 includes a drift tube assembly 53 that includes a drift tube 10 and an aperture grid 54, ion gate 56 and extractor grid 58 disposed therewithin. The ion mobility drift tube assembly 52 further includes an ion detector 60 and an ionization source 62.

The ion mobility drift tube assembly measures ions' mobility by directing analytes of interest introduced through port 66 to the ionization source by way of a carrier gas that is introduced through port 64 and exhausted through port 68. The resulting ionized analytes are extracted from the ionization source by the extractor grid and are directed down the drift tube towards the detector (opposite to the carrier gas flow direction) by the electric potential gradient created by the drift tube. The gate electrodes allow small pulses of ions to travel to the detector. The gate electrodes ensure that all the ions in an ion packet or pulse start at the same place in the electric field as they begin the mobility experiment, analogous to horses all starting a race in the starting gate instead of a staggered start. If the ion gate is 'leaky,' i.e. the ions do not all start the mobility experiment at the same time, the mobility peaks will be very broad and the mobility measurements will be poor.

The ions that comprise the ion pulse separate according to their mobility in an electric field and reach the detector at different, characteristic times. The electric field must be as uniform as possible over the diameter of the ion beam to ensure all ions travel the same distance to the detector. The aperture grid improves the resolving power of the ion mobility spectrometer by preventing the ions from inducing a charge on the detector and making the ion pulse appear wider than it is.

This induced charge is recorded on the detector along with the current caused by the ions itself, thus causing the width of the ion packet to be larger than it truly is and results in decreasing the resolving power of the IMS.

Figure 8A:
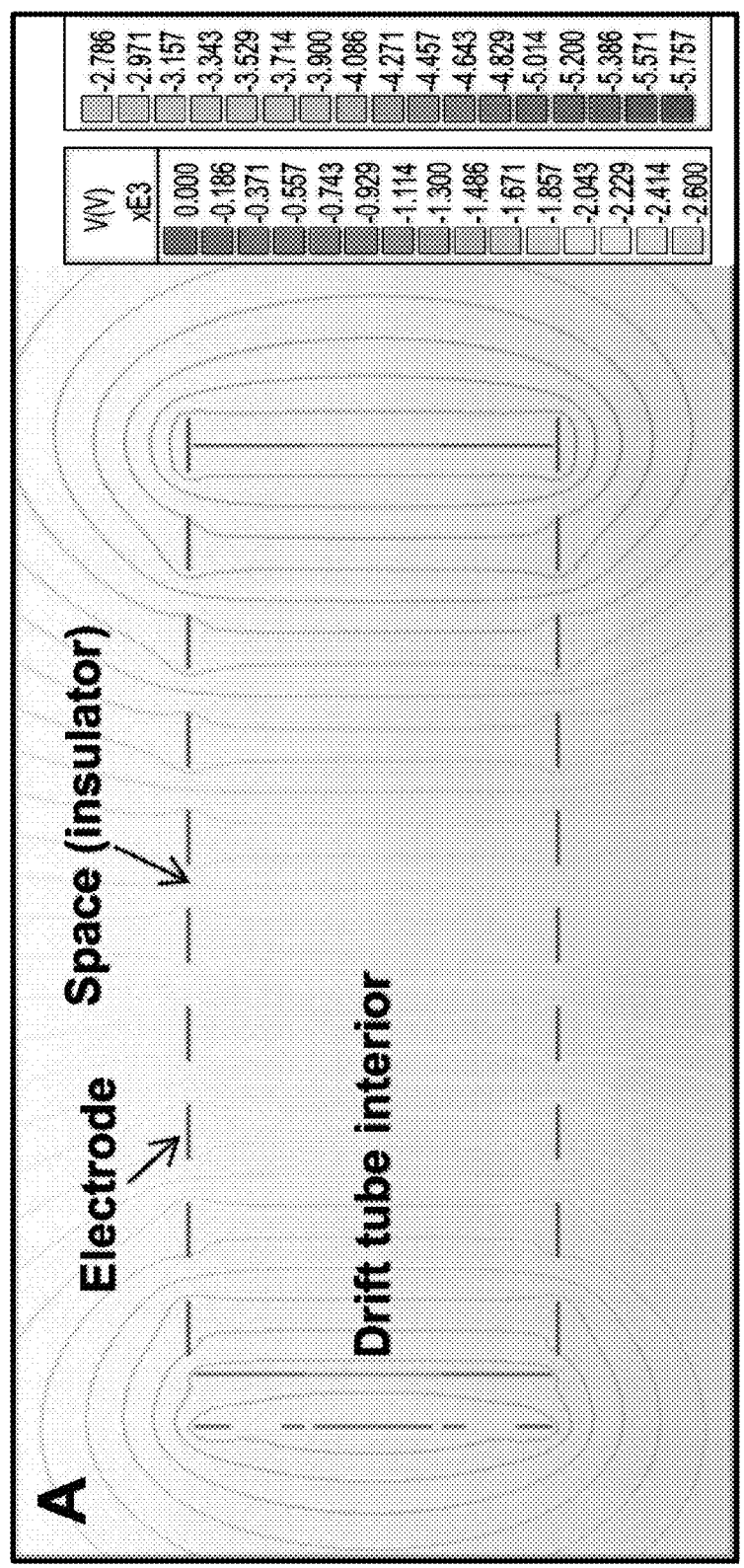
FIG. 8A illustrates electric field simulations of a stacked electrode/insulator drift tube when no external potential is present.
Figure 8B:
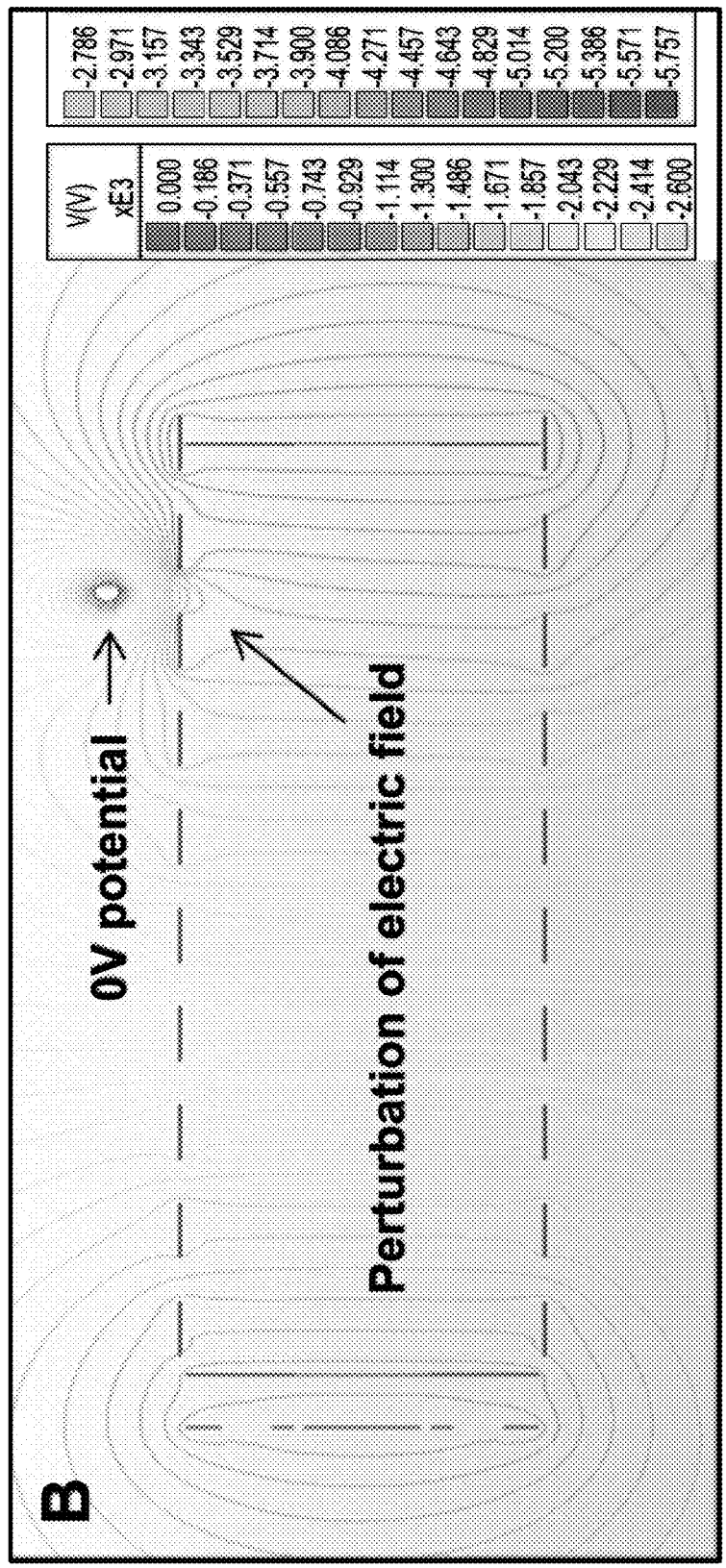
FIG. 8B illustrates electric field simulations of a stacked electrode/insulator drift tube when a 0V potential is present outside the drift tube. Perturbations of the electric field as shown by the curved field lines are clearly observed when the external potential is present.

FIG. 8A illustrates electric field simulations of a stacked electrode/insulator drift tube when no external potential is present. FIG. 8B illustrates electric field simulations of a stacked electrode/insulator drift tube when a 0V potential is present outside the drift tube. Perturbations of the electric field as shown by the curved field lines are clearly observed when the external potential is present. As can be seen by this comparison, the uniformity of the electric field inside the drift tube is disrupted creating non-uniform paths for ions to travel. This degrades the resolution of the analytical signal provided by the ion pulse.

Figure 9A:
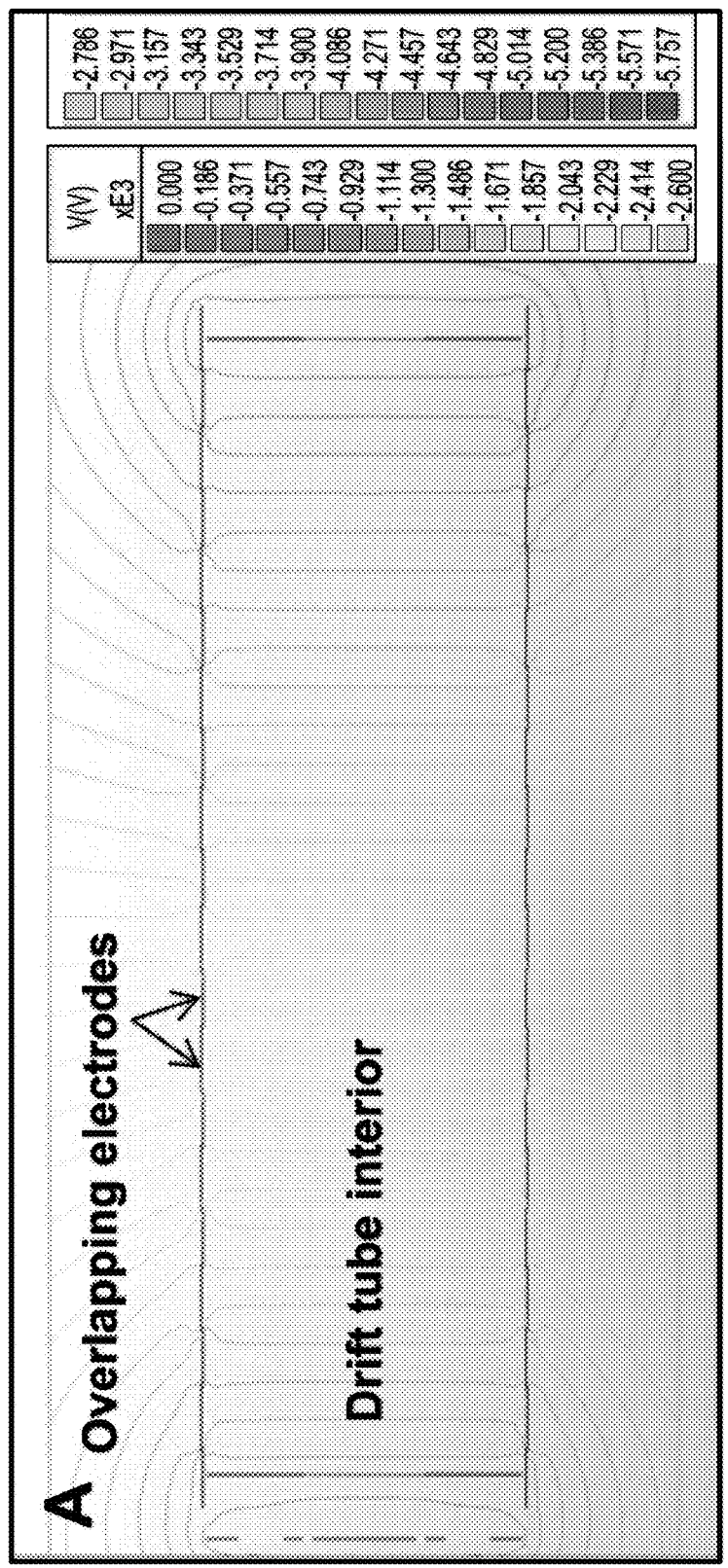
FIG. 9A illustrates electric field simulations showing the perturbations of the electric field inside self-shielding flex-circuit drift tube when no external potential is present nearby.
Figure 9B:
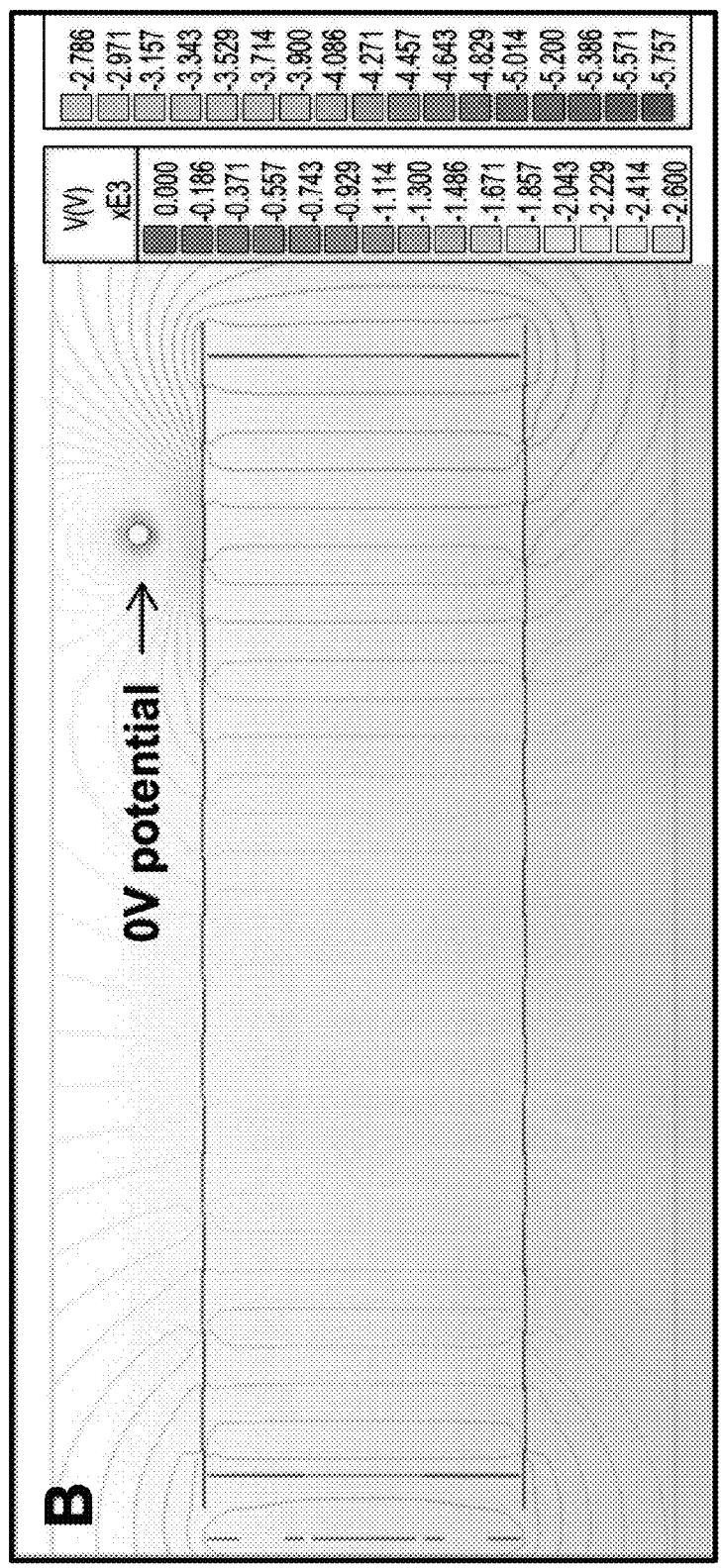
FIG. 9B illustrates electric field simulations showing the perturbations of the electric field inside self-shielding flex-circuit drift tube when a 0V external potential is present outside the drift tube. No perturbations of the electric field are observed when the external potential is present.

FIG. 9A illustrates electric field simulations showing the perturbations of the electric field inside self-shielding flex-circuit drift tube when no external potential is present nearby. FIG. 9B illustrates electric field simulations showing the perturbations of the electric field inside self-shielding flex-circuit drift tube when a 0V external potential is present outside the drift tube. No perturbations of the electric field are observed when the external potential is present. As can be seen by this comparison, the presence of external fields do not disrupt the electric field internal to the drift tube, demonstrating the ability of this design to shield the internal field from external EMI.

Figure 10:
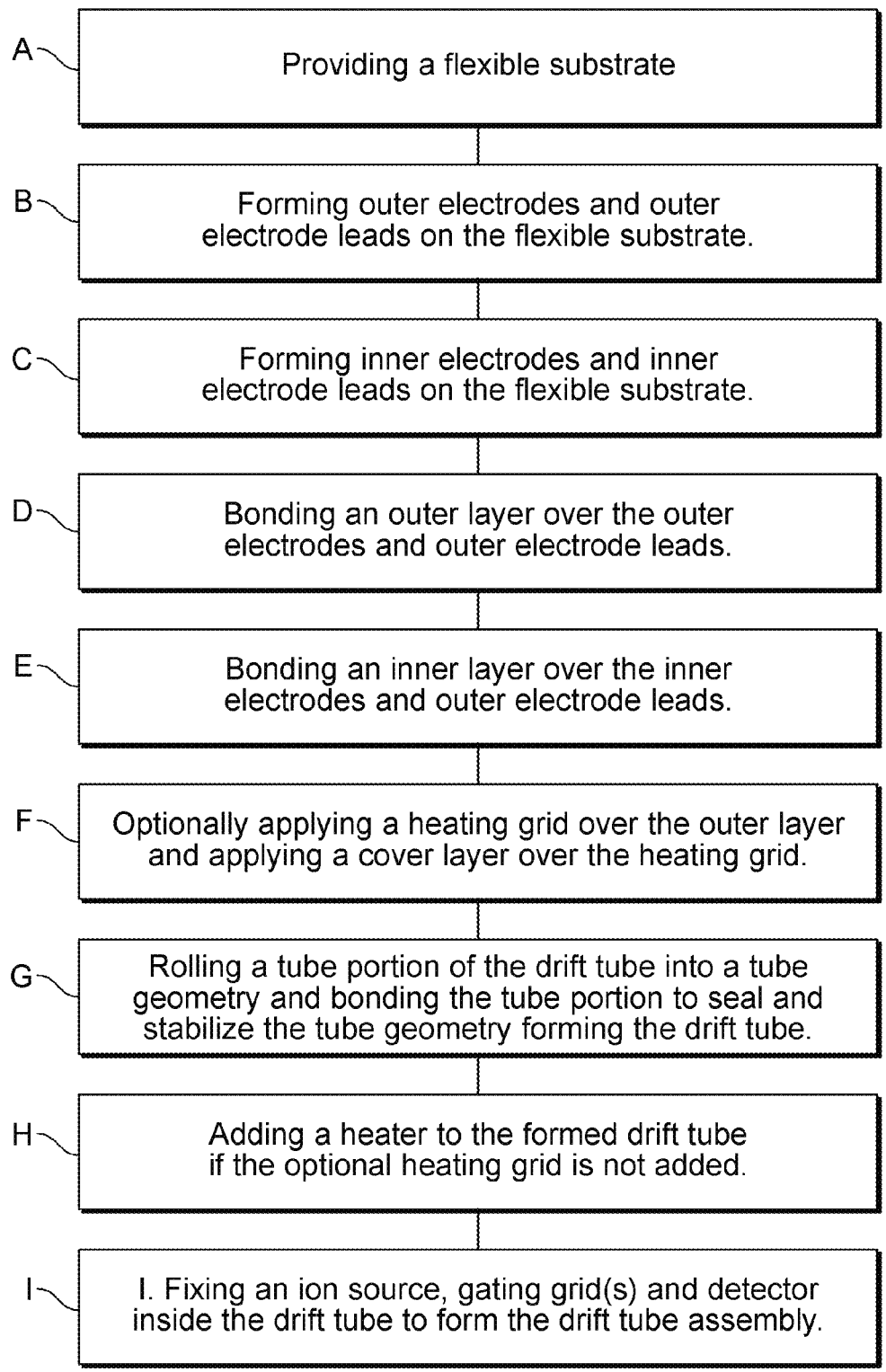
FIG. 10 shows an embodiment of a method of forming a drift tube and drift tube assembly according to the disclosure.

According to another embodiment of the disclosure, methods of forming a drift tube and a drift tube assembly are disclosed and summarized in FIG. 10 that include the following steps:

a. providing a flexible substrate
b. forming outer electrodes and outer electrode leads on the flexible substrate
c. forming inner electrodes and inner electrode leads on the flexible substrate
d. bonding an outer layer over the outer electrodes and outer electrode leads
e. bonding an inner layer over the inner electrodes and inner electrode leads
f. optionally applying an heating grid over the outer layer and applying a cover layer over the heating grid
g. rolling a tube portion of the drift tube into a tube geometry and bonding the tube portion to seal and stabilize the tube geometry forming the drift tube
h. adding a heater to the formed drift tube if the optional heating grid is not added
i. fixing an ion source, gating grid(s) and detector inside the drift tube to form the drift tube assembly.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

The invention is claimed as follows:

1. A drift tube, comprising:
   a tube portion comprising:
      a top, nonconductive layer;
      a flexible, nonconductive substrate comprising a top surface and a bottom surface;
      a bottom, nonconductive layer;
      wherein the flexible nonconductive substrate is disposed between the top, nonconductive layer and the bottom, nonconductive layer;
   a plurality of outer conductive electrodes disposed on and in contact with the top surface of the flexible, nonconductive substrate in the tube portion; and
   a plurality of inner conductive electrodes disposed on and in contact with the bottom surface of the flexible, nonconductive substrate in the tube portion.

2. The drift tube of claim 1, further comprising:
   a circuit leads portion adjacent the tube portion.

3. The drift tube of claim 2, further comprising:
   a plurality of outer electrode conductive leads electrically connected to the plurality of outer electrodes and disposed on the top surface of the substrate in the circuit leads portion; and
   a plurality of inner electrode conductive leads electrically connected to the plurality of inner electrodes and disposed on the bottom surface of the substrate in the circuit leads portion.

4. The drift tube of claim 1, wherein the flexible, nonconductive substrate is a polymer.

5. The drift tube of claim 1, further comprising:
   a heating element surrounding the top surface of the tube portion.

6. The drift tube of claim 5, wherein the heating element is a heater wire.

7. The drift tube of claim 5, wherein the heating element is an integral heater bonded to the flexible substrate.

8. The drift tube of claim 1, further comprising layers of a flexible, nonconductive material covering the plurality of outer and inner electrodes.

9. The drift tube assembly of claim 1, further comprising:
   an ion detector and extractor grid disposed at opposing ends of the drift tube.

10. A drift tube assembly, comprising:
    a drift tube, comprising:
       a tube portion, wherein the tube portion comprises:
          a top, nonconductive layer;
          a flexible, nonconductive substrate comprising a top surface, a bottom surface;
          a bottom, nonconductive layer;
          wherein the flexible nonconductive substrate is disposed between the top, nonconductive layer and the bottom, nonconductive layer;
          a plurality of outer electrodes disposed on and in contact with the top surface of the tube portion; and
          a plurality of inner electrodes disposed on and in contact with the bottom surface of the tube portion; and
    an aperture grid, ion gate and extractor grid disposed with the tube portion.

11. An ion mobility spectrometer comprising the drift tube assembly of claim 10.

12. A method of making a drift tube, comprising
    providing a flexible, nonconductive substrate comprising a top surface and a bottom surface;
    forming outer electrodes on the top surface and inner electrodes on the bottom surface of a tube portion of the flexible, nonconductive substrate;
    forming a top, nonconductive layer over the outer electrodes and top surface;
    forming a bottom, nonconductive layer over the inner electrodes and bottom surface; and
    forming the tube portion into a tube geometry having an inner central axis so that the top surface is further away from the inner central axis than the bottom surface.

13. The method of claim 12, wherein the flexible, nonconductive substrate further comprises
    a circuit leads portion adjacent the tube portion, and
    forming a plurality of outer electrode conductive leads electrically connected to the plurality of outer electrodes and disposed on the top surface of the substrate in the circuit leads portion; and
    forming a plurality of inner electrode conductive leads electrically connected to the plurality of inner electrodes and disposed on the bottom surface of the substrate in the circuit leads portion.

14. The method of claim 12, wherein the flexible, nonconductive substrate is formed of a polymer.

15. The method of claim 12, further comprising:
    forming a heating element around the top surface of the tube portion.

16. The method of claim 15, wherein the heating element is formed from a heater wire.

17. The method of claim 15, wherein the heating element is formed from an integral heater bonded to the flexible substrate.

18. The method of claim 12, further comprising:
    forming layers of a flexible, nonconductive material covering the plurality of outer and inner electrodes.

* * * * *